United States Patent [19]

Sillén et al.

[11] Patent Number: 5,672,154

[45] Date of Patent: Sep. 30, 1997

[54] METHOD AND APPARATUS FOR CONTROLLED INDIVIDUALIZED MEDICATION

[75] Inventors: Rudolf Vallentin Sillén, Ronneby; Göran Wessberg, Upsala, both of Sweden

[73] Assignee: MiniDoc i Uppsala AB, Upsala, Sweden

[21] Appl. No.: 387,943

[22] PCT Filed: Aug. 27, 1993

[86] PCT No.: PCT/SE93/00708

§ 371 Date: Feb. 27, 1995

§ 102(e) Date: Feb. 27, 1995

[87] PCT Pub. No.: WO94/06088

PCT Pub. Date: Mar. 17, 1994

[30] Foreign Application Priority Data

Aug. 27, 1992 [SE] Sweden ................................ 9202460

[51] Int. Cl.⁶ .............................................. A61M 31/00
[52] U.S. Cl. .............................. 604/50; 128/924; 395/924
[58] Field of Search .......................... 604/49, 50, 65–67; 395/924; 364/413.02

[56] References Cited

U.S. PATENT DOCUMENTS

| | | |
|---|---|---|
| 5,019,974 | 5/1991 | Beckers . |
| 5,126,957 | 6/1992 | Kaufman et al. . |
| 5,214,745 | 5/1993 | Sutherland ................................ 395/22 |
| 5,299,121 | 3/1994 | Brill et al. . |
| 5,327,355 | 7/1994 | Chiba et al. ........................ 395/915 X |
| 5,464,103 | 11/1995 | Lemelson ............................ 604/50 X |

FOREIGN PATENT DOCUMENTS

| | | |
|---|---|---|
| 0 128 054 | 12/1984 | European Pat. Off. . |
| 0 303 930 | 2/1989 | European Pat. Off. . |
| 2218831 | 11/1989 | United Kingdom . |

OTHER PUBLICATIONS

"A Neural Network Expert System for Diagnosing and Treating Hypertension" Riccardo Poli et al Mar. 1991 IEEE.
"The Effect of Noise on Concept Learning", Learning from Noisy Data, Machine Learning An Artificial Intelligence Approach, vol. II, J. Ross Quinlan, (1986) pp. 149–166, R.S. Michalski et al. (eds.).
"Discovering Rules by Induction From Large Collections of Examples, Introductory Readings in Expert Systems", J. Ross Quinlan, (D. Michie) pp. 168–201, (1979).
*Introductory Readings in Expert Systems Studies in Cybernetics*: 1, Gordon and Breach, pp. 196–197.
*On Machine Intelligence*, Ellis Horwood Series in Artificial Intelligence, second edition, Donald Michie, pp. 233–234.

*Primary Examiner*—Mark Bockelman
*Attorney, Agent, or Firm*—Burns, Doane, Swecker & Mathis, L.L.P.

[57] ABSTRACT

A method and a device for giving patients individualized, situation-dependent medication advice are disclosed. Preferably, the invention is implemented in portable computers. The method is founded on knowledge-based computer technology and comprises a reminder function (1), a recording and storage function (2, 3), as well as a function for inductive data analysis (4) and rule generation. When the knowledge-based system (6) finds that a medicine should be taken, the computer emits a signal providing information on the type of medicine and the dose. The patients records the intake of medicine as well as his current state of health. This information is stored in a database together with the point of time. Inductive data analysis is used to spot the relationship between various events and symptoms as well as establish medication rules. These rules are refined upon as new information is recorded in the database, and are automatically adapted to changes in the patient's state of health.

20 Claims, 1 Drawing Sheet

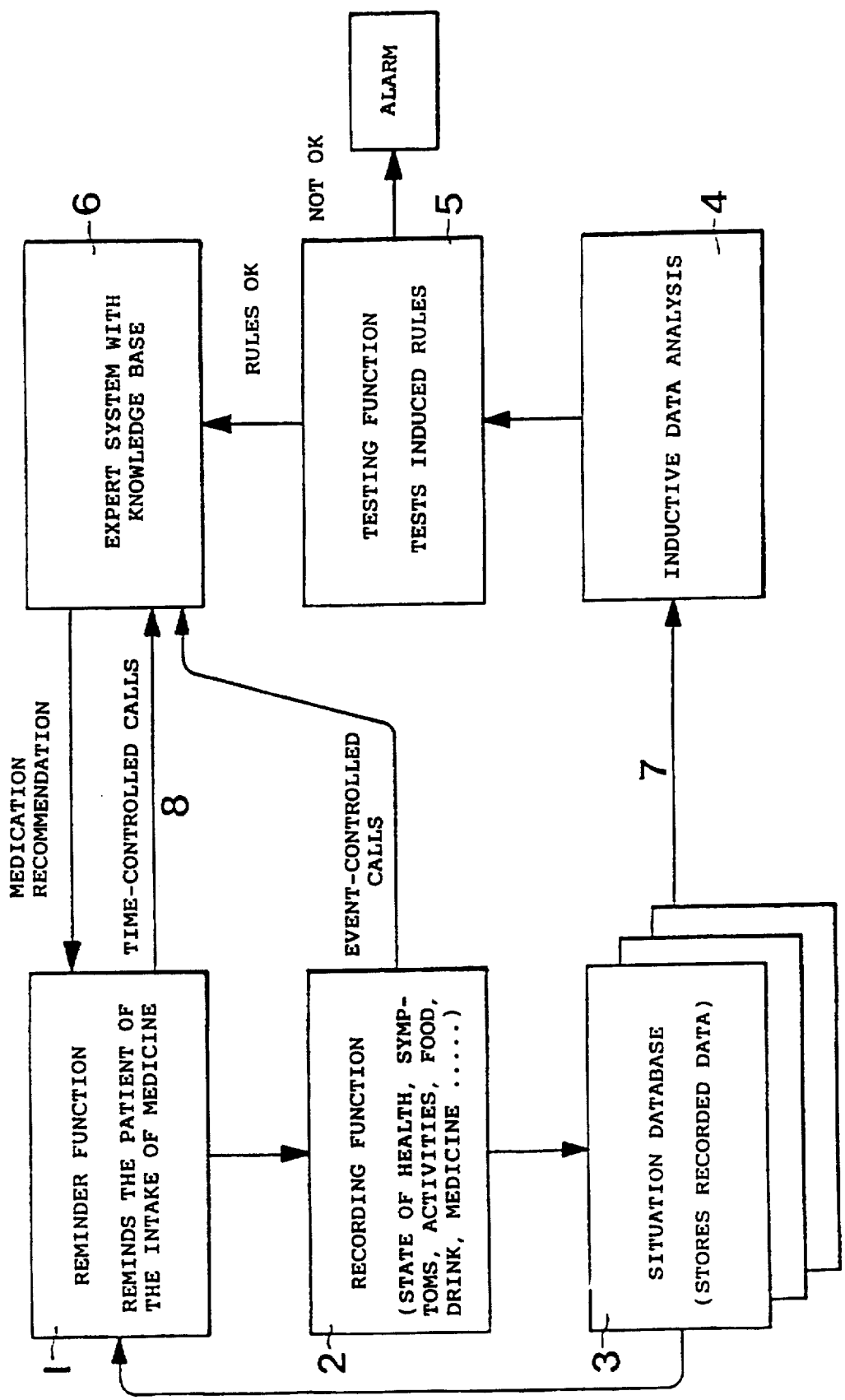

METHOD AND APPARATUS FOR CONTROLLED INDIVIDUALIZED MEDICATION

This application is a 371 of PCT/SE93/00708 filed Aug. 27, 1993, published as WO94/06088 Mar. 17, 1994.

BACKGROUND OF THE INVENTION

This invention relates to a method for controlled individualised medication.

FIELD OF THE INVENTION

Many chronic diseases in man require the administration of various substances in order to counteract the disease and/or to keep down its symptoms. Medication often includes several different pharmaceutical preparations, each having its specific properties, duration of action, and so forth. Dosage and time intervals between administrations depend on the status of the disease, patient-specific factors, such as inheritance, age, weight, general state of health as well as diet and physical activities. As a result, medication is a fairly complicated task to perform. In practice, this will manifest itself as variations in the patient's state of health. In the case of some diseases, such as Parkinson's disease, the symptoms may in a single day vary from making the patient incapacitated for work (rigidity, tremor, etc.) to leaving the patient almost untroubled.

There are several different methods used for providing recommendations as to the dosage and the time intervals between administrations. These recommendations are often founded on the adjustment of an initial concept based on pharmacokinetic information on the various preparations. The adjustments are made on the basis of recordations of the patient's condition on various occasions. This information is interpreted by specialists, and used for adjusting the dosage and the time intervals.

However, the methods currently used do not yield desirable results, the reason being that the pharmacokinetic effects of the preparations are not absolutely clear. The way the preparations move through the body is affected by interactions with other preparations, enzymes and so forth, during the absorption and the distribution phase as well as during the metabolism and the secretion phase. Thus, the actual concentration of a preparation in the biophase, the duration of action and the effect cannot be predicted statistically using monotonic models. Another reason is that the evaluation of the patient's data is a complex operation since it involves many dependent variables and since it further is difficult to lay down analytical models.

It is likely that the state of health of certain groups of patients can be drastically improved by optimum, individualised and situation-dependent medication. This would result in enhanced quality of life, as well as fewer sickness pensioners.

GB 2,218,831 teaches an apparatus for helping people suffering from chronic diseases, such as diabetes, to determine medication doses and keep a suitable diet, thereby to improve their state of health. This apparatus has a key pad for entering data on the blood glucose levels as well as the physical activity of the patient, a memory where e.g. data on the prescribed dosage are stored, a program for computing suitable doses of insulin on the basis of inputted data as well as data stored in the memory, and a display for showing the doses of insulin computed.

Similar apparatus are described in U.S. Pat. No. 5,019,974 and EP Patent Application 0 128 054.

These prior-art apparatus are all based on there being a known relationship between a condition of the patient, such as the blood glucose level, and the well-being of the patient, and on the medication having a known effect on the patient. Thus, one may establish fixed medication rules valid for comparatively long periods of time.

However, in the case of other chronical diseases, such as Parkinson's disease, epilepsy and abnormal blood pressures, there does not exist any single actual value or condition of the patient that can be measured and correlated with the well-being of the patient. For these diseases, medication generally includes several medicines, whose precise interactions and effects on the patient are not fully known. In addition, the health condition of the patient is affected by a plurality of external factors. Thus, it is impossible to establish fixed medication rules valid for long periods of time, and the prior-art apparatus therefore cannot be used for controlled individualised medication in the treatment of more complicated diseases.

SUMMARY OF THE INVENTION

The object of the present invention is to provide a method and a device for controlled, individualised medication in the treatment of complicated diseases whose mechanisms are not fully known, thereby to improve the patient's state of health.

This object is attained by a method and a device having the distinctive features recited in appended claims 1 and 9, respectively. Other features of the invention are stated in the appended subclaims.

The invention has the great advantage of automatically drawing conclusions from the inputted data as to what activities, what external factors and what medication will result in a satisfactory state of health for the patient. On the basis of these conclusions, rules are established regarding when and in what doses the different medicines are to be taken. The thus-established rules are not fixed, but are continuously refined upon with the aid of data recorded by the patient. Thus, the invention gradually "learns" what is needed for the well-being of the patient. Further, the rules are automatically adapted to changes in the patient without the device reprogramming.

BRIEF DESCRIPTION OF THE DRAWING

The invention will be described in more detail below with reference to the accompanying drawing, which schematically illustrates the structure of a device in accordance with the invention.

DETAILED DESCRIPTION OF THE PREFERRED EMBODIMENTS

The aim of the invention is to give the patients controlled, individualised and situation-dependent medication advice, thereby to optimize the patient's sense of well-being. The inventive method is adaptive, i.e the basic rules for the advice are altered if the relevant factors affecting the patient are changed. Conveniently, the invention is implemented in portable "wallet-size" computers.

As appears from the drawing, the method is founded on a knowledge-based computer system or expert system 6 communicates with, is associated with, and otherwise has access to a reminder function 1, a recording and storage function 2, 3, as well as a function 4 for inductive rule generation.

When the system is operating, the reminder function block 1 cause the computer to emit a signal when a pharmaceutical preparation is to be taken (or some other activity is to be performed), and which indicates the type of preparation to be taken as well as the dosage. The recording function block 2 of the system allows the patient to confirm that medicine has been taken, and to indicate his current state of health by responding to questions put to him by the computer. In addition, the patient records other relevant events, such as awakening, intake of food, exercise and stress, as they occur.

These data are stored in a database 3 together with the point of time at issue. Optionally, some of such data be automatically retrieved by sensors.

The information stored in situation database 3, is used to determine relevant relations in time between various events and to generate examples different symptoms are to be controlled. The examples consist of values for the relevant (affecting factors), as well as an associated symptom value (conclusion). The attributes used to determine each medication are, among others, "current dosage", "time from intake", and "remaining duration of action".

Collections of examples are automatically created every day for each group of symptoms. These collections are accumulated in a "rolling" database, preferably including examples from the last 20 days. The examples are then used in each group of symptoms for spotting, with the aid of prior-art inductive data analysis 4, the relationships that exist, and drafting rules for predicting the effect on the symptoms by various dosages of medications.

Inductive data analysis and rule generation are described in, inter alia, the following publications: Quinlan, J. R. (1979), Discovering Rules by Induction from Large Collections of Examples, Introductory Readings in Expert Systems (D. Michie), pp 33–46, London; Gordon and Breach 1979. Quinlan, J. R. (1983), Learning from Noisy Data, Proceedings of the International Machine Learning Workshop, University of Illinois, pp 58–64, 1986.

The prediction rules are generated in the form of decision trees and/or so-called conditional rules of the type:

If X1<0.12 and Z3="protein B" AND Z1>0.34 AND Z2=2 THEN RIGIDITY="excessive agility".

The rules are validated at testing block 5 by comparing the proposed rules to known thresholds drawn from long-term experience. Approved rules are transferred to the knowledge base of expert system 6 in known manner. The expert system may be a conventional rule-based system or be based on fuzzy logic. The approved rules stored in expert system 6 can predict a patient's overall state of health with predictions of the various symptoms in a specific situation.

When in use, the expert system 6 is automatically accessed in indicated at 8 at regular time intervals, preferably every five minutes. When called, the rules stored in system are consulted using the current values from the situation database 3. During consultation, time data are preferably delayed by a expected elapsed time factor corresponding to the time from the intake of a medication to the attainment of its biophase. This enables the system to signal before any undesirable effects appear (early warning system). The consultation is performed in known manner via "backward chaining", i.e. starting from a desirable conclusion (state of health). Desirable conclusions can be predetermined for every group of symptoms.

The expert system 6 operates in real time and can, in each specific situation, quickly determine the prerequisites and conditions necessary to achieve the desired state of health.

If this state cannot be achieved in a specific situation (e.g. because the patient has forgotten to act on previous advice), the system looks for the prerequisites for attaining a "second-best" state of health. Induction of rules and updating of the knowledge base are performed automatically by the system, conveniently once every twenty-fourth hours. Because the expert system 6 detects patterns by inductive analysis of real situations, individualised medication recommendations can be provided without requiring explicit causal connections or pharmacological data. The prerequisite being that the attributes used directly or indirectly represent patterns that can be classified. According to the invention, the patient records the point of time when he takes the various medications, the dosage, as well as his current state of health. These data are used for generating, by inductive data analysis, the prediction rules stored in expert system 6 that are used to provide advice on the point of time and the dosage.

For each medication, one starts from a patient-specific longest nominal duration of action. In the examples, the remaining duration of action as well as the dosage of the current and the previous dosages are determined. Other relevant factors, such as the intake of food, state of stress and related time, are also included in the examples.

The prediction rules generated by prior-art inductive data analysis block 4 and stored in expert system 6 are called at predetermined intervals, and delayed by a time delay, which preferably corresponds to the elapsed time from intake to the attainment of the biophase. The prediction rules are called by backward chain, based on the current situation and the desired state of health. If any of the conditions that can be influenced is not satisfied, e.g. the dosage of a preparation, the system will recommend that this be done.

A mode of operation of the invention, intended for controlled, individualised adaptive medication in the treatment of Parkinson's disease, will be described below. In Parkinson's disease, the body cannot produce sufficient amounts of a neurotransmitter in the brain called dopamine, which results in limitations of movement, muscular cramp and tremor. This state can be counteracted by the supply of various preparations, such as L-dopa, which are converted to dopamine or the substance bromokriptin. In order to master undesirable side-effects, such as effects on the blood pressure, these preparations generally have to be combined with other medicines. Thus, medication frequently involves at least three different preparations, each having a specific dosage and a specific time interval between administrations. Owing to the interactions taking place, the time intervals and the doses have to be adapted to one another. Also external factors, such as the intake of food, exercise and state of stress, affect the action of the preparations. As a result, patients that have been ill for a long time, and thus have had plenty of time to find which medication suits them best, are seldom perfectly untroubled for a whole day. Frequently, there are two or more periods during the day in which they experience considerable discomfort in the form of tremor, rigidity and "dullness of mind". Too low a dosage typically results in tremor, rigidity and muscular cramp. Discomfort caused by overdosage manifests itself in the form of uncontrolled excessive agility, among other things. The reminder function block 1 in the inventive system indicates when the preparations, such as Pravidel, Sinemet, Inderal, Madopark, and Eldepryl, are to be taken, and further provides recommendations as to the intake of liquid, food and rest.

The recording function block 2 includes compulsory input of the state of health expressed as degrees of the attributes "Rigidity", "Agility", "Tremor" and "Dullness of Mind".

Recordation is also performed when other important events take place, such as "awakening", "falling asleep", "eating" and "drinking". In recordation, time is indicated in minutes from awakening.

When generating examples, the times elapsing from the intake of the various preparations and events to the present time are determined. Two times are preferably determined for each preparation, namely the time that has elapsed from the previous intake and the time that has elapsed from the current intake.

A nominal duration of action from the intake is used for the various preparations. When the individual duration of action is known, this is indicated.

At the end of each day, a collection of examples with attribute values determined as above is created and stored in a database 3. The recorded state of health is indicated as a conclusion for each example.

A collection of examples is thus made for each of the indicated states of health, i.e. one collection of examples with the conclusion related to "Rigidity", one collection related to "Tremor", and one collection related to "Dullness of Mind". Then, rules are induced from the collections of examples by inductive analysis block 4, and the rules are validated (in testing block 5) by comparing their threshold values with indicated maximum and minimum limits as to dosage and time.

If a rule falls outside these limits, the indicated limit values are used.

Thereafter, the rules are transferred to the knowledge base in the deductive expert system 6.

The generation of examples, the induction and the transfer to the database are automatically initiated at the end of each day.

When using the system, the reminder function block 1 is activated when the patient starts the computer upon awakening.

The reminder function block 1 calls the expert system 6 at intervals of preferably about 5 minutes, and the expert system 6 is thus consulted with respect to the data recorded. In consultation, an advance time corresponding to the average time elapsing from the intake of a preparation to its commenced action, is added to the real time. Preferably, the advance time is 30 min. Consequently, the system will be able to issue reminders in good time.

We claim:

1. A method for determining a patient-specific medication regimen, comprising the steps of:

recording a first type of patient-specific information, including a type of medicine, a dosage, and a point of time in a database each time a patient ingests medicine;

recording a second type of patient-specific information describing a state of health of the patient at predetermined intervals in the database;

performing an inductive analysis of the patient-specific information recorded in the database to generate patient-specific proposed medication rules based on detected relationships between the patient's intake of medicine and the patient's state of health;

comparing the patient-specific proposed medication rules with one or more predetermined thresholds for approval, and storing approved rules; and recalling the approved rules to decide whether medication is desired based on the patient's current state of health and, if so, a recommended type of medicine and a recommended dosage.

2. A method as set forth in claim 1, wherein the recommended type of medicine includes at least two different medicines.

3. A method as set forth in claim 2, further comprising the step of recording a third type of patient-specific information on the patient's intake of food and the patient's activities in the database prior to the step of performing the inductive analysis.

4. A method as set forth in claim 2, wherein the step of recording the second type of patient-specific information describing the patient's state of health is performed each time the step of recording the patient's intake of medicine is performed.

5. A method as set forth in claim 2, further comprising the step of recording supplemental patient-specific data prior to the step of performing the inductive analysis, the supplemental patient-specific data including the patient's awakening, intake of food, exercise, or stress, wherein the proposed medication rules are further based on relations in time between the recorded supplemental patient-specific data and the state of health recorded.

6. A method as set forth in claim 2, further comprising the steps of allotting a duration of action to each medicine; and continuously calculating the remaining duration of action of each medicine.

7. A method as set forth in claim 6, wherein the proposed medication rules are further based on the dosage and the remaining duration of action.

8. A method as set forth in claim 2, wherein the controlled individualized dosage of medicine is used for the treatment of Parkinson's disease.

9. A method as set forth in claim 1, further comprising the step of recording a third type of patient-specific information on the patient's intake of food and his activities in the database prior to the step of performing the inductive analysis.

10. A method as set forth in claim 9, wherein the step of recording the second type of patient-specific information describing the patient's state of health is performed each time the step of recording the patient's intake of medicine is performed.

11. A method as set forth in claim 9, further comprising the step of recording supplemental patient-specific data prior to the step of performing the inductive analysis, the supplemental patient-specific data including the patient's awakening, intake of food, exercise, or stress, wherein the proposed medication rules are further based on relations in time between the recorded supplemental patient-specific data and the state of health recorded.

12. A method as set forth in claim 9, further comprising the steps of allotting a duration of action to each medicine; and continuously calculating the remaining duration of action of each medicine.

13. A method as set forth in claim 12, wherein the proposed medication rules are further based on the dosage and the remaining duration of action.

14. A method as set forth in claim 1, wherein the step of recording the second type of patient-specific information describing the patient's state of health is performed each time the step of recording the patient's intake of medicine is performed.

15. A method as set forth in claim 14, further comprising the step of recording supplemental patient-specific data prior to the step of performing the inductive analysis, the supplemental patient-specific data including the patient's awakening, intake of food, exercise, or stress, wherein the proposed medication rules are further based on relations in time between the recorded supplemental patient-specific data and the state of health recorded.

16. A method as set forth in claim 1, further comprising the step of recording supplemental patient-specific data prior to the step of performing the inductive analysis, the supplemental patient-specific data including the patient's awakening, intake of food, exercise, or stress, wherein the proposed medication rules are further based on relations in time between the recorded supplemental patient-specific data and the state of health recorded.

17. A method as set forth in claim 1, further comprising the steps of allotting a duration of action to each medicine; and continuously calculating the remaining duration of action of each medicine.

18. A method as set forth in claim 17, wherein the proposed medication rules are further based on the dosage and the remaining duration of action.

19. A method as set forth in claim 1, wherein the controlled individualized dosage of medicine is used for the treatment of Parkinson's disease.

20. A device for controlled, individualised medication, characterised by means (2) for recording information on the intake of medicine and the patient's state of health, a database (3) for storing this information, a program (4) for performing an inductive analysis of the information stored in the database and establishing medication rules on the basis of detected relationships between the intake of medicine and the patient's state of health, memory means (5) for storing predetermined medication conditions, means (5) for comparing the medication rules established by means of the program for performing inductive analysis and the predetermined medication conditions for approval of the medication rules, an expert system (6) where the approved rules are used for deciding whether medication is to be performed and, if so, which type of medicine and what dose should be given, means (7) for activating the program for inductive analysis at given points of time, and means (8) for polling the expert system at given points of time.

* * * * *